United States Patent
Gunderson et al.

(10) Patent No.: US 6,638,719 B1
(45) Date of Patent: Oct. 28, 2003

(54) GENOTYPING BIALLELIC MARKERS

(75) Inventors: Kevin Gunderson, San Diego, CA (US); David J. Lockhart, Del Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/603,999

(22) Filed: Jun. 26, 2000

Related U.S. Application Data

(60) Provisional application No. 60/143,633, filed on Jul. 14, 1999.

(51) Int. Cl.[7] .............................. C12Q 1/68; C12P 19/34; C07H 21/04
(52) U.S. Cl. .............................. 435/6; 435/4; 435/91.1; 435/91.2; 536/23.1; 536/23.5; 536/24.3; 536/24.33
(58) Field of Search ........................... 435/6, 91.2, 816; 536/24.3, 24.33

(56) References Cited

U.S. PATENT DOCUMENTS

| | | | |
|---|---|---|---|
| 5,639,611 A | * 6/1997 | Wallace et al. | ................ 435/6 |
| 5,700,637 A | 12/1997 | Southern | |
| 5,837,832 A | * 11/1998 | Chee et al. | ................ 536/22.1 |
| 5,981,176 A | * 11/1999 | Wallace | ....................... 435/6 |
| 6,013,449 A | * 1/2000 | Hacia et al. | ................... 435/6 |
| 6,287,778 B1 | * 9/2001 | Huang et al. | .................. 435/6 |
| 6,368,799 B1 | * 4/2002 | Chee | ............................. 435/6 |

FOREIGN PATENT DOCUMENTS

WO 89/10977 11/1989

OTHER PUBLICATIONS

Stratagen Catalog (1988).*
Tobe et al. "Single–well genotyping of diallelic sequence variations by a two–color ELISA–based eligonucleotide ligation assay" Nucleic Acids Research, 1996, vol. 24, No. 19.

* cited by examiner

*Primary Examiner*—Kenneth R. Horlick
*Assistant Examiner*—Alexander H. Spiegler
(74) *Attorney, Agent, or Firm*—Banner & Witcoff, Ltd.

(57) ABSTRACT

A method is described for determining the genotype of one or more individuals at a biallelic marker. The method employs amplification of a region of genomic DNA using color tagged, allele-specific primers and hybridization of the products to an array of allele-specific probes. The genotype is identified from the pattern of hybridization.

9 Claims, 1 Drawing Sheet

REPRESENTS CROSS-HYBRIDIZATION IN A/A AND A/G EXAMPLES, BUT REPRESENTS CROSS-PCR IN G/G EXAMPLE.

REPRESENTS CROSS-HYBRIDIZATION IN G/G AND A/G EXAMPLES, BUT REPRESENTS CROSS-PCR IN A/A EXAMPLE.

GENOTYPING BIALLELIC MARKERS

This application claims the benefit of provisional application Ser. No. 60/143,633, filed Jul. 14, 1999, which is incorporated by reference herein.

FIELD OF THE INVENTION

The invention is related to the area of genome analysis. In particular it is related to the field of identification of genotypes.

BACKGROUND OF THE INVENTION

Obtaining genotype information on thousands of biallelic markers in a highly parallel fashion is increasingly becoming an important task in mapping disease loci, in indentifying quantitative trait loci, in diagnosing tumor loss of heterozygocity, and in performing association studies. A currently available method for simultaneously obtaining large numbers of biallelic marker genotypes involves hybridization to allele-specific probes on high density oligonucleotide arrays. In order to practice that method, redundant sets of hybridization probes, typically twenty or more, are used to score each biallelic marker. A high degree of redundancy is required to reduce noise and achieve an acceptable level of accuracy. Even this level of redundancy is insufficient to unambiguously score heterozygotes or to quantitatively determine allele frequency in a population. Because of these limitations, there is a need in the art for more reliable and more quantitative methods to identify genotypes at biallelic markers.

SUMMARY OF THE INVENTION

It is an object of the invention to provide methods and compositions for analysis of variations in genomic DNA. These and other objects of the invention are provided by one or more of the embodiments described below.

One embodiment of the invention provides a method for determining the genotype of one or more individuals at a biallelic marker. The method comprises the step of amplifying a region of double stranded DNA comprising a biallelic marker to form an amplified DNA product using a first and a second pair of primers. The first pair of primers specifically amplifies a first allelic form of the biallelic marker and the second pair of primers specifically amplifies a second allelic form of the biallelic marker. Each pair of primers comprises an upstream and a downstream primer. Each upstream primer is complementary to a strand of the DNA which is opposite to a strand of the DNA to which the downstream primer is complementary. Each upstream primer is labeled with a color tag; the first upstream primer is labeled with a first color tag and the second upstream primer is labeled with a second color tag. The upstream primer of the first primer pair terminates in a 3' nucleotide which is complementary to the first allelic form but not complementary to the second allelic form. The upstream primer of the second primer pair terminates in a 3' nucleotide which is complementary to the second allelic form but not complementary to the first allelic form. The method further comprises the step of hybridizing the amplified DNA product to at least two probes which are immobilized to known locations on a solid support. A first probe is complementary to the first allelic form and a second probe is complementary to the second allelic form of the biallelic marker. A unique pattern of hybridization is formed on the solid support, which permits differentiation of and quantification of heterozygotes from homozygotes for the biallelic marker.

Another embodiment of the invention provides a set of primers for use in determining the genotype of an individual at a biallelic marker. The set of primers comprises a first pair of primers which specifically amplifies a first allelic form of the biallelic marker and a second pair of primers which specifically amplifies a second allelic form of the biallelic marker. Each pair of primers comprises an upstream and a downstream primer. Each upstream primer is complementary to a strand of the DNA which is opposite to a strand of the DNA to which the downstream primer is complementary. Each upstream primer is labeled with a color tag; the first upstream primer is labeled with a first color tag and the second upstream primer is labeled with a second color tag. The upstream primer of the first primer pair terminates in a 3' nucleotide which is complementary to the first allelic form but not complementary to the second allelic form. The upstream primer of the second primer pair terminates in a 3' nucleotide which is complementary to the second allelic form but not complementary to the first allelic form.

Still another embodiment of the invention provides a kit comprising in a single container two or more sets of primers as described in the preceding paragraph.

Yet another embodiment of the invention provides a kit comprising in a single container a set of primers as described above and a solid support comprising at least two probes which are immobilized to known locations on the solid support A first probe is complementary to a first allelic form and a second probe is complementary to a second allelic form of a biallelic marker.

The invention thus provides the art with methods and compositions for identification of genotypes in a DNA sample from one or more individuals.

Figure 1:
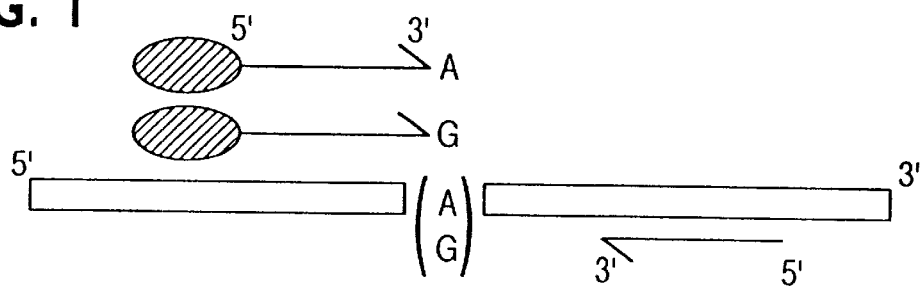
FIG. 1 illustrates the design of allele-specific PCR primers for biallelic markers. The two upstream primers are chosen such that one primer complementary to the "A" allele is labeled with a 5' red tag, and the other primer complementary to the "G" allele is labeled with a 5' green tag. The downstream primer, which can be the same for both upstream primers, is chosen as close to the allele-specific upstream primers as possible given the constraints of good primer design.

Three examples are shown: A/A homozygote, G/G homozygote, and A/G heterozygote. Notice that cross-hybridization can be distinguished from cross-amplification noise by the two-color intensity patterns.

DETAILED DESCRIPTION OF THE INVENTION

It is a discovery of the present inventors that genotyping of biallelic markers can be accomplished with great certainty by hybridizing uniquely tagged allele-specific nucleic acid sequences to allele-specific probes in an array. A nucleic acid sample is amplified by allele-specific amplification so as to uniquely label each allele of a biallelic marker which is present in the sample. Each allele can be labeled with a different color tag, for example. The use of a different tag for each allele eliminates the confusion between cross-hybridization and cross-amplification which arises with a single tag. Such confusion can prevent unambiguous or reliable assignment of genotypes.

For any organism, each gene encodes a single molecular species of protein or RNA. An organism possesses one or more copies of each gene. A diploid organism, for example, possesses two copies of each type of autosomal gene in its somatic cells. Each type of gene exists in a population of organisms as several variants, known as alleles. The "genotype" of an individual organism is the description of the particular complement of alleles at a given genetic locus, and "genotyping" refers to the act of determining the genotype of one or more individual organisms. A "biallelic marker" is a unique sequence within a genome that exhibits two distinct alleles, usually differing by a single base substitution. "Determining the genotype of a biallelic marker" refers to determining which of two possible alleles is present in an individual, e.g., on each of the two homologous chromosomes of a diploid organism.

Allele-specific amplification of a nucleic acid sample uses distinctively labeled, allele-specific primers. The amplification products for each allele, which incorporate the distinctively labeled primers, are hybridized to an array comprising allele-specific probes. The genotype for each biallelic marker can then be determined from the spatial and color pattern of hybridization. In addition, if the nucleic acid sample is derived from a population or group of individual organisms, the frequency of each allele of a biallelic marker can be quantified using the hybridization pattern. A plurality of biallelic markers in a given nucleic acid sample can be simultaneously analyzed using a plurality of sets of primers and one or more arrays of allele-specific probes.

The genotype of one or more individuals or organisms can be determined at a biallelic marker. A region of double stranded DNA comprising a biallelic marker is amplified to form an amplified DNA product. The DNA can be of any source, including genomic, nuclear, cDNA, mitochondrial DNA, macronuclear DNA, and micronuclear DNA. The amplification is accomplished using a first and a second pair of primers. Any type of amplification reaction can be used, including PCR, ligase chain reaction, transcription amplification, and self-sustained sequence replication. Thus, appropriate enzymes such as DNA polymerase or DNA ligase will be used as desired by the artisan. The first pair of primers specifically amplifies a first allelic form of the biallelic marker and the second pair of primers specifically amplifies a second allelic form of the biallelic marker. The biallelic marker is likely a substitution mutation but may comprise a deletion or insertion. Each pair of primers comprises an upstream and a downstream primer. Each upstream primer is complementary to a strand of the DNA which is opposite to a strand of the DNA to which the downstream primer is complementary. Each upstream primer is labeled with a color tag; the first upstream primer is labeled with a first color tag and the second upstream primer is labeled with a second color tag. Color tags are labels which are detectable and distinct, either visually or optically. The upstream primer of the first primer pair terminates in a 3' nucleotide which is complementary to the first allelic form but not complementary to the second allelic form. The upstream primer of the second primer pair terminates in a 3' nucleotide which is complementary with the second allelic form but not complementary to the first allelic form.

The amplified DNA product can be hybridized to at least two probes which are immobilized to known locations on a solid support. A first probe is complementary to the first allelic form and a second probe is complementary to the second allelic form of the biallelic marker. A unique spatial and visual pattern of hybridization is formed on the solid support, which permits differentiation of and quantification of heterozygotes from homozygotes for the biallelic marker. The first color tag and the second color tag can be optically detected on the solid support. The quantities of the first and second color tags at known locations on the solid support can be compared and the genotype can be determined of the one or more individuals or organisms from whom the double stranded DNA was obtained.

The genotype of two or more biallelic markers can be determined simultaneously. The amplification can be done in one or more reaction vessels. The hybridization can be done using allele-specific probes in the same array or different arrays.

A set of primers for use in determining the genotype of a biallelic marker comprises a first pair of primers which specifically amplifies a first allelic form of the biallelic marker and a second pair of primers which specifically amplifies a second allelic form of the biallelic marker. Each pair of primers comprises an upstream and a downstream primer. Each upstream primer is complementary to a strand of the DNA which is opposite to a strand of the DNA to which the downstream primer is complementary. Each upstream primer is labeled with a color tag; the first upstream primer is labeled with a first color tag and the second upstream primer is labeled with a second color tag. The upstream primer of the first primer pair terminates in a 3' nucleotide which is complementary to the first allelic form but not complementary to the second allelic form. The upstream primer of the second primer pair terminates in a 3' nucleotide which is complementary to the second allelic form but not complementary to the first allelic form.

Two or more sets of primers can be supplied together in a single container as a kit. The container may be subdivided and may contain multiple vessels. So long as the components are physically attached to each other they form a ket. Such kits can additionally include a solid support comprising at least two probes, where each probe is complementary to a different allele of a biallelic marker. Instructions for use, enzymes for amplification, buffers and control samples can be included as components in the kit.

Further description of the embodiments is provided below.

Providing a Nucleic Acid Sample

The terms "nucleic acid" or "nucleic acid molecule" refer to a deoxyribonucleotide or ribonucleotide polymer in either single-or double-stranded form, and unless otherwise limited, would encompass analogs of a natural nucleotide that can function in a similar manner as naturally occurring nucleotide. One of skill in the art will appreciate that it is desirable to have nucleic acid samples containing target nucleic acid sequences that reflect the biallelic markers of interest. Therefore, suitable nucleic acid samples can contain biallelic markers of interest. Suitable nucleic acid samples, however, can also contain nucleic acids derived from the biallelic markers of interest. As used herein, a nucleic acid derived from a biallelic marker refers to a nucleic acid for whose synthesis the genomic DNA containing the biallelic marker or a subsequence thereof has ultimately served as a template. Thus, a DNA amplified from genomic DNA, an RNA transcribed from the amplified DNA, an mRNA transcribed from the genomic DNA, or a CDNA reverse transcribed from the mRNA, etc., are all derived from the biallelic marker, and detection of such derived products is indicative of the presence and/or abundance of the original biallelic marker in a sample. Thus, suitable samples include, but are not limited to, isolated genomic DNA containing the gene or genes containing the biallelic marker, an RNA transcript derived from the isolated genomic DNA, cDNA reverse transcribed from the transcript, cRNA transcribed from the cDNA, DNA amplified from the genes, RNA transcribed from amplified DNA, and the like.

The nucleic acid sample can be a homogenate of cells or tissues or other biological samples. Preferably, the nucleic acid sample is a total DNA preparation of a biological sample. More preferably in some embodiments, the nucleic acid sample is the total genomic DNA isolated from a biological sample. The nucleic acid sample can be the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature MRNA, RNA processing intermediates, nascent transcripts or degradation intermediates.

Biological samples can be of any biological tissue or fluid or cells from any organism. Frequently the sample will be a "clinical sample," which is a sample derived from a patient. Clinical samples provide a rich source of information regarding the various alleles of a gene and their relation to disease. Some embodiments of the invention can be employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples can also include sections of tissues, such as frozen sections or formalin-fixed sections taken for histological purposes. Cell cultures are another typical source of biological samples. Cell cultures used as a source of DNA or RNA can be derived from a clinical sample, or can be supplied from a primary cell culture, a subculture, or a cell line from any organism.

Allele-Specific Amplification

The nucleic acid sample is subjected to amplification prior to hybridization and detection of an allelic marker. Methods for amplification of a nucleic acid are well known in the art. In general, amplification of a nucleic acid employs a pair of single-stranded oligonucleotide primers together with an enzyme, e.g., DNA polymerase, which replicates (amplifies) the nucleic acid, resulting in multiple copies of the region delimited by the sequences that are complementary to the primers. A preferred amplification method is allele-specific amplification. Okayama et al., *J Lab. Clin. Med.* 114:105–113 (1989). In allele-specific amplification, the single nucleotide substitution which is characteristic of a given allele is placed at the 3' end of one of the primers. Only that allele which is complementary to the primer will be amplified; another allele, which contains a different single nucleotide substitution and is not complementary to the 3' end of the primer, will not be amplified. The amplification reaction itself can be carried out according to the polymerase chain reaction (PCR) (see *PCR Protocols, A Guide to Methods and Applications*, Innis et al., Academic Press, Inc. N.Y., (1990)) or another suitable amplification method. Other suitable amplification methods include, but are not limited to ligase chain reaction (LCR) (see Wu and Wallace, *Genomics*, 4: 560 (1989); Landegren, et al., *Science*, 241: 1077 (1988); and Barringer, et al., *Gene*, 89: 117 (1990)), transcription amplification (Kwoh, et al., *Proc. Natl. Acad. Sci. USA*, 86: 1173 (1989)), and self-sustained sequence replication (Guatelli, et al., *Proc. Nat. Acad. Sci. USA*, 87: 1874 (1990)).

One of skill in the art will appreciate that whatever amplification method is used, if a quantitative result is desired, care must be taken to use a method that maintains or controls for the relative frequencies of the amplified nucleic acids to achieve quantitative amplification. Methods of quantitative amplification are well known to those of skill in the art. For example, quantitative PCR may involve simultaneously co-amplifying a known quantity of a control sequence using the same primers used to amplify the nucleic acids of interest. This provides an internal standard that can be used to calibrate the PCR reaction. The high density array can then include probes specific to the internal standard for quantification of the amplified nucleic acid. Detailed protocols for quantitative PCR are provided in *PCR Protocols, A Guide to Methods and Applications*, Innis et al. Academic Press, Inc. N.Y., (1990).

Primer Design

Allele-specific amplification requires a particular pair of primers for each given allele to be identified. Detection of both alleles of a biallelic marker therefore requires a set of two pairs of primers, one for each allele of the biallelic marker. The set of primers comprises a first pair of primers which specifically amplifies a first allelic form of the biallelic marker and a second pair of primers which specifically amplifies a second allelic form of the biallelic marker.

Each pair of primers comprises an upstream and a downstream primer (FIG. 1). The terms "upstream" and "downstream" refer to the orientation of each primer with respect to the nucleotide substitution which is characteristic of a given allele. The upstream primer is complementary to a region of genomic DNA and can be, but need not be, located 5' to the nucleotide substitution of the allele. The downstream primer is complementary to a region of genomic DNA and can be, but need not be, located 3' to the nucleotide substitution of the same allele. Each upstream primer is complementary to a strand of the DNA which is opposite to a strand of the DNA to which the downstream primer is complementary. The upstream primer of the first primer pair terminates in a 3' nucleotide which is complementary to the first allelic form but not complementary to the second allelic form. The upstream primer of the second primer pair terminates in a 3' nucleotide which is complementary to the second allelic form but not complementary to the first allelic form.

Each upstream primer is labeled with a "color tag". The color tag can be a fluorescent label (e.g., fluorescein, texas red, rhodamine, green fluorescent protein, and the like) or other label as defined under "Signal Detection" below. The first upstream primer is labeled with a first color tag and the second upstream primer is labeled with a second color tag. The first and second color tags are distinguishable from each other upon detection. For example, the first and second color tags can be two different fluorescent labels with distinct excitation and/or emission wavelengths.

Hybridizing Nucleic Acids to Arrays of Allele-Specific Probes

"Hybridization" refers to the formation of a bimolecular complex of two different nucleic acids through complementary base pairing. Complementary base pairing occurs through non-covalent bonding, usually hydrogen bonding, of bases that specifically recognize other bases, as in the bonding of complementary bases in double-stranded DNA. In this invention, hybridization is carried out between a target nucleic acid, which is prepared from the nucleic acid sample by allele-specific amplification, and at least two probes which have been immobilized on a substrate to form an array.

One of skill in the art will appreciate that an enormous number of array designs are suitable for the practice of this invention. An array will typically include a number of probes that specifically hybridize to the sequences of interest. Allele-specific probes are preferred in this invention. An allele-specific probe is a probe that specifically hybridizes to a sequence specific for an allele of interest. In addition, it is preferred that the array include one or more control probes. In one embodiment, the array is a high density array. A high density array is an array used to hybridize with a target nucleic acid sample to detect the presence of a large number of allelic markers, preferably more than 10, more preferably more than 100, and most preferably more than 1000 allelic markers.

High density arrays are suitable for quantifying small variations in the frequency of an allelic marker in the presence of a large population of heterogeneous nucleic acids. Such high density arrays can be fabricated either by de novo synthesis on a substrate or by spotting or transporting nucleic acid sequences onto specific locations of a substrate. Both of these methods produce nucleic acids which are immobilized on the array at particular locations. Nucleic acids can be purified and/or isolated from biological materials, such as a bacterial plasmid containing a cloned segment of a sequence of interest. Suitable nucleic acids can also be produced by amplification of templates or by synthesis. As a nonlimiting illustration, polymerase chain reaction, and/or in vitro transcription are suitable nucleic acid amplification methods.

The term "target nucleic acid" refers to a nucleic acid (either synthetic or derived from a biological sample or nucleic acid sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term "target nucleic acid" can refer to the specific subsequence of a larger nucleic acid to which the probe is directed or to the overall sequence (e.g., gene or MRNA) whose presence it is desired to detect. The difference in usage will be apparent from context.

As used herein a "probe" is defined as a nucleic acid, capable of binding to a target nucleic acid of complementary sequence through one or more types of chemical bonds, usually through complementary base pairing, usually through hydrogen bond formation. As used herein, a probe can include natural (i.e. A, G, U, C, or T) or modified bases (e.g., 7-deazaguanosine, inosine, etc.). A probe can also include an oligonucleotide. An oligonucleotide is a single-stranded nucleic acid of 2 to n bases, where n can be any integer less than 1000. Nucleic acids can be cloned or synthesized using any technique known in the art. They can also include non-natually occurring nucleotide analogs, such as those which are modified to improve hybridization, and peptide nucleic acids. In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

Probe Design

An array includes "test probes." Test probes can be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 to 25 nucleotides in length. In another embodiment, test probes are double or single stranded DNA sequences. DNA sequences can be isolated or cloned from natural sources or amplified from natural sources using natural nucleic acids as templates. However, in situ synthesis of probes on the arrays is preferred. The probes have sequences complementary to particular subsequences of the genes whose allelic markers they are designed to detect. Thus, the test probes are capable of specifically hybridizing to the target nucleic acid they are designed to detect. Test probes which are allele-specific probes are capable of hybridizing specifically to a given allele.

The term "perfect match probe" refers to a probe which has a sequence that is perfectly complementary to a particular target sequence. The probe is typically perfectly complementary to a portion (subsequence) of the target sequence. The perfect match probe can be a "test probe," a "normalization control probe," an expression level control probe and the like. A perfect match control or perfect match probe is, however, distinguished from a "mismatch control" or "mismatch probe" or "mismatch control probe."

In addition to test probes that bind the target nucleic acid(s) of interest, the high density array can contain a number of control probes. The control probes fall into two categories: normalization controls and mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency, and other factors that may cause the signal of a perfect hybridization to vary between arrays. In a preferred embodiment, signals (e.g., fluorescence intensity) read from all other probes in the array are divided by the signal (e.g., fluorescence intensity) from the control probes, thereby normalizing the measurements.

Virtually any probe can serve as a normalization control. However, it is recognized that hybridization efficiency varies with base composition and probe length. Preferred normalization probes are selected to reflect the average length of the other probes present in the array; however, they can be selected to cover a range of lengths. The normalization control(s) can also be selected to reflect the (average) base composition of the other probes in the array; however in a preferred embodiment, only one or a few normalization probes are used and they are selected such that they hybridize well (i.e. no secondary structure) and do not match any target-specific probes.

Mismatch controls can also be provided for the probes to the target alleles or for normalization controls. The terms "mismatch control" or "mismatch probe" or "mismatch control probe" refer to a probe whose sequence is deliberately selected not to be perfectly complementary to a particular target sequence. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C, or a T for an A) at any of positions 6 through 14 (the central mismatch).

For each mismatch control in a high-density array there typically exists a corresponding perfect match probe that is perfectly complementary to the same particular target sequence. The mismatch may comprise one or more bases. While the mismatch(es) may be located anywhere in the mismatch probe, terminal mismatches are less desirable, as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

Mismatch probes provide a control for non-specific binding or cross-hybridization to a nucleic acid in the sample other than the target to which the probe is directed. Mismatch probes thus indicate whether or not a hybridization is specific. For example, if the target is present, the perfect match probes should be consistently brighter than the mismatch probes. The difference in intensity between the perfect match and the mismatch probe ($I_{(PM)}-I_{(MM)}$) provides a good measure of the concentration of the hybridized material.

Allele-specific probes will preferentially contain the single nucleotide substitution characteristic of the allele in a central position similar to a central mismatch in a mismatch control probe. In a preferred embodiment, both alleles of a biallelic marker are represented by allele-specific probes. Each allelespecific probe can be, for example, a perfect match probe for one allele of a biallelic marker. Both alleles can be represented by adjacent probes in the array. Furthermore, each allele-specific probe can serve as a mismatch control probe for the other. Alternatively, other mismatch control probes, which are not complementary to the sequence of either allele of the biallelic marker, can be used in the array. The pattern of specific hybridization to the two allele-specific probes of a biallelic marker can be used to derive the genotype of the organism that was the source of the nucleic acid pool.

The array can also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is from a eukaryote.

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20-mer sequence complementary to an IL-2 MRNA. However, there may exist 20-mer subsequences that are not unique to the IL-2 MRNA. Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and excluded either in the high density array itself (e.g.,during fabrication of the array) or in the post-hybridization data analysis.

Where antisense RNA or another antisense nucleic acids are used as the target nucleic acid pool, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Where the nucleic acid-pool is double stranded, the probes can be of either sense as the target nucleic acids, including both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., *Gene*, 88: 25–36 (1990)).

Forming High Density Arrays

High density arrays are particularly useful for monitoring the presence of allelic markers. The fabrication and application of high density arrays in gene expression monitoring have been disclosed previously in, for example, WO 97/10365, WO 92/10588, U.S. application Ser. No. 08/772, 376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposes by reference. In some embodiments using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified.

Synthesized oligonucleotide arrays are particularly preferred for this invention. Oligonucleotide arrays have numerous advantages over other methods, such as efficiency of production, reduced intra- and inter array variability, increased information content, and high signal-to-noise ratio.

Preferred high density arrays comprise greater than about 100, preferably greater than about 1000, more preferably greater than about 16,000, and most preferably greater than 65,000 or 250,000 or even greater than about 1,000,000 different oligonucleotide probes, preferably in less than 1 cm$^2$ of surface area. The oligonucleotide probes range from about 5 to about 50 or about 500 nucleotides, more preferably from about 10 to about 40 nucleotides, and most preferably from about 15 to about 40 nucleotides in length.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523, which disclose methods of forming vast arrays of peptides, oligonucleotides and other molecules using, for example, light-directed synthesis techniques. See also, Fodor et al., *Science*, 251, 767–77 (1991). These procedures for synthesis of polymer arrays are now referred to as VLSIPSTM procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPST™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, eg., Pirrung et al. U.S. Pat. No. 5,143,854. Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

Additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, can be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer "B" is coupled to second selected regions, some of which can be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthezied or natural nucleic acids in predetermined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

Hybridization Conditions

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH.

The $T_m$ is the temperature, under defined ionic strength, pH, and nucleic acid concentration, at which 50% of the probes complementary to the target sequence hybridize to the target sequence at equilibrium. As the target sequences are generally present in excess, at $T_m$, 50% of the probes are occupied at equilibrium). Typically, stringent conditions will be those in which the salt concentration is at least about 0.01 to 1.0 M concentration of a Na or other salt at pH 7.0 to 8.3 and the temperature is at least about 30° C. for short probes (e.g., 10 to 50 nucleotides). Stringent conditions can also be achieved with the addition of destabilizing agents such as formamide.

The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) of DNA or RNA. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency.

Conversely, at higher stringency (e.g., higher temperature or lower salt) successful hybridization requires fewer mismatches.

One of skill in the art will appreciate that hybridization conditions can be selected to provide any degree of stringency. In a preferred embodiment, hybridization is performed at low stringency, in this case in 6×SSPE-T at 37° C. (0.005% Triton X-100), to ensure hybridization, and then subsequent washes are performed at higher stringency (e.g., 1×SSPE-T at 37° C.) to eliminate mismatched hybrid duplexes. Successive washes can be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity can be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array can be washed at successively higher stringency solutions and read between each wash. Analysis of the data sets thus produced will reveal a wash stringency above which the hybridization pattern is not appreciably altered and which provides adequate signal for the particular oligonucleotide probes of interest.

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have two hydrogen bonds per base-pair, while the G-C duplexes have three hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature.

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol. 24: Hybridization With Nucleic Acid Probes*, P. Tijssen, ed. Elsevier, N.Y., (1993)).

Signal Detection

The hybridized nucleic acids can be detected by detecting one or more labels attached to the target nucleic acids. The labels can be incorporated by any of a number of means well known to those of skill in the art. However, in a preferred embodiment, the label is incorporated by labeling the primers prior to the amplification step in the preparation of the target nucleic acids. Thus, for example, polymerase chain reaction with labeled primers will provide a labeled amplification product.

According to the invention, the allele-specific primers for a biallelic marker are prepared such that the primer for amplification of one allele is distinguishable upon detection from the primer for the the other allele. Consequently, the amplification products corresponding to the two alleles can also be distinguised. In a preferred embodiment, the primers are labeled by covalently attaching a fluorescent label at or near their 5' ends, and the primer for each allele is labeled with a moiety possessing a distinct excitation and/or emission wavelength. Thus, in one embodiment, each allele will emit light of a characteristic color which can be optically detected, i.e., detected by any optical means capable of distinguishing between the light produced by the different color tags used and capable of assigning the signal from each probe to the corresponding allele.

Detectable labels suitable for use in the present invention include any composition detectable by spectroscopic, photochemical, biochemical, immunochemical, electrical, optical, or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^{3}$H, $^{125}$I, $^{35}$S, $^{14}$C, or $^{32}$P), enzymes (e.g., horseradish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. One method uses colloidal gold label that can be detected by measuring scattered light.

The label can be added to the target nucleic acids prior to, or after the hybridization. So called "direct labels" are detectable labels that are directly attached to or incorporated into the target nucleic acids prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid can be biotinylated before the hybridization. After hybridization, an avidin-conjugated fluorophore will bind the biotin-bearing hybrid duplexes, providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Means of detecting labeled target nucleic acids hybridized to the probes of the array are known to those of skill in the art. Thus, for example, where a calorimetric label is used, simple visualization of the label is sufficient. Where a radioactive labeled probe is used, detection of the radiation (e.g. with photographic film or a solid state detector) is sufficient.

Detection of target nucleic acids which are labeled with a fluorescent label (i.e., a "color tag") can be accomplished with fluorescence microscopy. The hybridized array can be excited with a light source at the excitation wavelength of the particular fluorescent label and the resulting fluorescence at the emission wavelength is detected. The excitation light source can be a laser appropriate for the excitation of the fluorescent label.

The confocal microscope can be automated with a computer-controlled stage to automatically scan the entire high density array, i.e., to sequentially examine individual probes or adjacent groups of probes in a systematic manner until all probes have been examined. Similarly, the microscope can be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application 20 92/10092, and copending U.S. application Ser. No. 08/195,889, filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

Two different fluorescent labels can be used in order to distinguish two alleles at each biallelic marker examined. In such a case, the array can be scanned two times. During the first scan, the excitation and emission wavelengths are set as required to detect one of the two fluorescent labels. For the second scan, the excitation and emission wavelengths are set as required to detect the second fluorescent label. When the results from both scans are compared, the genotype identification or allele frequency can be determined.

Quantification and Determination of Genotypes

The term "quantifying" when used in the context of quantifying hybridization of a nucleic acid sequence or subsequence can refer to absolute or to relative quantification. Absolute quantification can be accomplished by inclusion of known concentration(s) of one or more target nucleic acids (e.g., control nucleic acids such as Bio B, or known amounts the target nucleic acids themselves) and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, the frequency of an allele. Relative quantification can also be used to merely detect the presence or absence of an allele in the target nucleic acids. In one embodiment, for example, the presence or absence of the two alleles of a biallelic marker can be determined by comparing the quantities of the first and second color tag at the known locations in the array, i.e., on the solid support, which correspond to the allele-specific probes for the two alleles.

A preferred quantifying method is to use a confocal microscope and fluorescent labels. The GeneChipo system (Affymetrix, Santa Clara, Calif.) is particularly suitable for quantifying the hybridization; however, it will be apparent to those of skill in the art that any similar system or other effectively equivalent detection method can also be used.

Methods for evaluating the hybridization results vary with the nature of the specific probes used, as well as the controls. Simple quantification of the fluorescence intensity for each probe can be determined. This can be accomplished simply by measuring signal strength at each location (representing a different probe) on the high density array (e.g., where the label is a fluorescent label, detection of the florescence intensity produced by a fixed excitation illumination at each location on the array).

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value can be selected below which a signal is counted as being essentially indistinguishable from background.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target allele, for the lowest 5% to 10% of the probes for each allele. However, where the probes to a particular allele hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g., probes directed to nucleic acids of the opposite sense or to genes not found in the sample, such as bacterial genes where the sample is mammalian nucleic acids). Background can also be calculated as the average signal intensity produced by regions of the array that lack any probes at all. In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra).

The high density array can include mismatch controls. In a preferred embodiment, there is a mismatch control having a central mismatch for every probe in the array, except the normalization controls. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control show high signals, or the mismatch shows a higher signal than its corresponding test probe, there is a problem with the hybridization and the signal from those probes is ignored. For a given biallelic marker, the difference in hybridization signal intensity ($I_{allele1}-I_{allele2}$) between an allele-specific probe (perfect match probe) for a first allele and the corresponding probe for a second allele (or other mismatch control probe) is a measure of the presence of or concentration of the first allele. Thus, in a preferred embodiment, the signal of the mismatch probe is subtracted from the signal for its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored (i.e., the signal cannot be evaluated).

Figure 2:
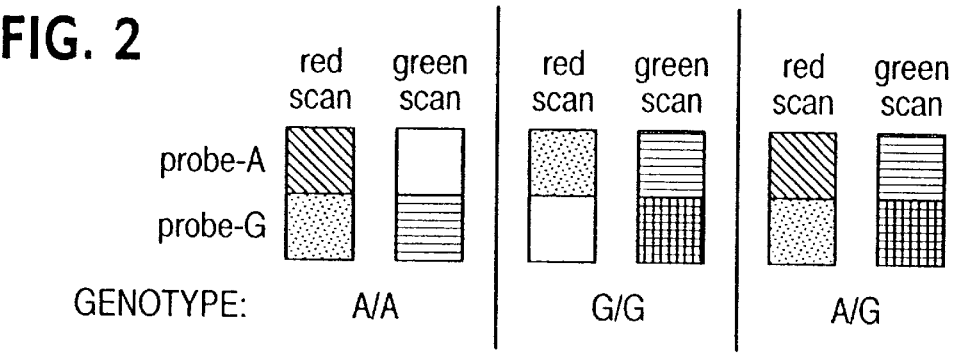
FIG. 2 demonstrates detection of the amplicons on a simple genotyping array using two scan colors (probe A complements allele A and probe G complements allele G where the substitution difference is centrally located).
Figure 2:
Figure 2:

For each biallelic marker analyzed, the genotype can be unambiguously determined by comparing the hybridization patterns obtained for each of the two labels, e.g., color tags employed (FIG. 2). If hybridization is indicated for one color tag to its corresponding allele-specific probe (e.g., "A") but not for the other color tag (e.g., "G") (pattern at left in FIG. 2), then the indicated genotype of a diploid organism would be homozygous A/A. If hybridization is indicated only for the other color tag to its corresponding allele-specific probe (e.g., "G") (pattern at center in FIG. 2), then the indicated genotype of a diploid organism would be homozygous G/G. If hybridzation is indicated for both color tags to their corresponding allele-specific probes (pattern at right in FIG. 2), then the indicated genotype of a diploid organism would be heterozygoous (A/G).

Marginal detection of hybridization, indicated by an intermediate positive result (e.g., less than 1%, or from 1–5%, or from 1–10%, or from 2–10%, or from 5–10%, or from 1–20%, or from 2–20%, or from 5–20%, or from 10–20% of the average of all positive hybridization results obtained for the entire array) may indicate either cross-hybridization or cross-amplification, depending on the overall hybridization pattern as indicated in FIG. 2. However, these can be distinguished by the unique pattern observed. See FIG. 2.

Further procedures for data analysis are disclosed in U.S. application Ser. No. 08/772,376, previously incorporated for all purposes.

Determination of Allele Frequency

"Allele frequency" is the frequency with which a given allele exists within a population or selected group of organisms.

It is understood that the examples and embodiments described herein are for illustrative purposes only and that various modifications or changes will be suggested to persons skilled in the art and are to be included within the spirit and purview of this application and scope of the appended claims. All publications, patents, and patent applications cited herein are hereby incorporated by reference for all purposes.

We claim:

1. A method to aid in determining a ratio of alleles at a polymorphic locus in a sample, comprising the steps of:
   (a) amplifying a region of double stranded DNA in a sample, wherein the region comprises a polymorphic locus to form amplified DNA products using a first and a second pair of primers, wherein the first pair of primers specifically amplifies a first allelic form of the polymorphic locus and the second pair of primers specifically amplifies a second allelic form of the polymorphic locus, wherein each pair of primers comprises an upstream and a downstream primer, wherein each upstream primer is complementary to a strand of the DNA which is opposite to a strand of the DNA to which the downstream primer is complementary, wherein each upstream primer is labeled with a color tag, wherein the first upstream primer is labeled with a first color tag and the second upstream primer is labeled with a second color tag, wherein the upstream primer of the first primer pair terminates in a 3' nucleotide which is complementary to the first allelic form but not complementary to the second allelic form, wherein the upstream primer of the second primer pair terminates in a 3' nucleotide which is complementary with the second allelic form but not complementary to the first allelic form;
   (b) hybridizing the amplified DNA products to at least two probes which are immobilized to known locations on a solid support, wherein a first probe is complementary to the first allelic form and a second probe is complementary to the second allelic form of the polymorphic locus, whereby a pattern of hybridization is formed on the solid support; and
   (c) determining a pattern of positive and intermediate-positive hybridizations to the first and second probes, wherein
      (i) cross-amplification is indicated if positive hybridization of the first color tag to the first probe is observed and intermediate-positive hybridization of the second color tag to the second probe is observed at a level of from 1–20% of the average of all positive hybridizations on the solid support;
      (ii) cross-amplification is indicated if positive hybridization of the second color tag to the second probe is observed and intermediate-positive hybridization of the first color tag to the first probe is observed at a level of from 1–20% of the average of all positive hybridizations on the solid support;
      (iii) cross-hybridization is indicated if positive hybridization of the first color tag to the first probe is observed and intermediate-positive hybridization of the first color tag to the second probe is observed at a level of from 1–20% of the average of all positive hybridizations on the solid support;
      (iv) cross-hybridization is indicated if positive hybridization of the second color tag to the second probe is observed and intermediate-positive hybridization of the second color tag to the first probe is observed at a level of from 1–20% of the average of all positive hybridizations on the solid support; and
      (v) cross hybridization is indicated if positive hybridization of the first color tag to the first probe and positive hybridization of the second color tag to the second probe, and either intermediate-positive hybridization of the second color tag to the first probe at a level of from 1–20% of the average of all positive hybridizations on the solid support, or intermediate-positive hybridization of the first color tag to the second probe at a level of from 1–20% of the average of all positive hybridizations on the solid support are observed, whereby hybridization patterns determined in step (c) aid in determining a ratio of alleles at the polymorphic locus.

2. The method of claim 1 further comprising the step of:
   optically detecting the first color tag and the second color tag on the solid support.

3. The method of claim 2 further comprising the step of:
   comparing quantities of first and second color tag at known locations on the solid support; and determining a ratio of alleles in the sample.

4. The method of claim 3, wherein the ratio of alleles at two or more polymorphic loci is determined simultaneously.

5. The method of claim 1, wherein the double stranded DNA is obtained from two or more individuals.

6. The method of claim 1, wherein two or more regions of double stranded DNA, each of which comprises a polymorphic locus, are amplified.

7. The method of claim 1, wherein
   (i) cross-amplification is indicated if positive hybridization of the first color tag to the first probe is observed and intermediate-positive hybridization of the second color tag to the second probe is observed at a level of from 5–20% of the average of all positive hybridizations on the solid support;
   (ii) cross-amplification is indicated if positive hybridization of the second color tag to the second probe is observed and intermediate-positive hybridization of the first color tag to the first probe is observed at a level of from 5–20% of the average of all positive hybridizations on the solid support;
   (iii) cross-hybridization is indicated if positive hybridization of the first color tag to the first probe is observed and intermediate-positive hybridization of the first color tag to the second probe is observed at a level of from 5–20% of the average of all positive hybridizations on the solid support;
   (iv) cross-hybridization is indicated if positive hybridization of the second color tag to the second probe is observed and intermediate-positive hybridization of the second color tag to the first probe is observed at a level of from 5–20% of the average of all positive hybridizations on the solid support; and
   (v) cross hybridization is indicated if positive hybridization of the first color tag to the first probe, positive hybridization of the second color tag to the second probe, intermediate-positive hybridization of the second color tag to the first probe at a level of from 5–20% of the average of all positive hybridizations on the solid support, and intermediate-positive hybridization of the first color tag to the second probe at a level of from 5–20% of the average of all positive hybridizations on the solid support are observed.

8. The method of claim 1, wherein
   (i) cross-amplification is indicated if positive hybridization of the first color tag to the first probe is observed and intermediate-positive hybridization of the second color tag to the second probe is observed at a level of from 2–20% of the average of all positive hybridizations on the solid support;
   (ii) cross-amplification is indicated if positive hybridization of the second color tag to the second probe is observed and intermediate-positive hybridization of the first color tag to the first probe is observed at a level of from 2–20% of the average of all positive hybridizations on the solid support;
   (iii) cross-hybridization is indicated if positive hybridization of the first color tag to the first probe is observed and intermediate-positive hybridization of the first color tag to the second probe is observed at a level of from 2–20% of the average of all positive hybridizations on the solid support;
   (iv) cross-hybridization is indicated if positive hybridization of the second color tag to the second probe is observed and intermediate-positive hybridization of the second color tag to the first probe is observed at a level of from 2–20% of the average of all positive hybridizations on the solid support; and
   (v) cross hybridization is indicated if positive hybridization of the first color tag to the first probe, positive hybridization of the second color tag to the second probe, intermediate-positive hybridization of the second color tag to the first probe at a level of from 2–20% of the average of all positive hybridizations on the solid support, and intermediate-positive hybridization of the first color tag to the second probe at a level of from 2–20% of the average of all positive hybridizations on the solid support are observed.

9. The method of claim 1, wherein
   (i) cross-amplification is indicated if positive hybridization of the first color tag to the first probe is observed and intermediate-positive hybridization of the second color tag to the second probe is observed at a level of from 10–20% of the average of all positive hybridizations on the solid support;
   (ii) cross-amplification is indicated if positive hybridization of the second color tag to the second probe is observed and intermediate-positive hybridization of the first color tag to the first probe is observed at a level of from 10–20% of the average of all positive hybridizations on the solid support;
   (iii) cross-hybridization is indicated if positive hybridization of the first color tag to the first probe is observed and intermediate-positive hybridization of the first color tag to the second probe is observed at a level of from 10–20% of the average of all positive hybridizations on the solid support;
   (iv) cross-hybridization is indicated if positive hybridization of the second color tag to the second probe is observed and intermediate-positive hybridization of the second color tag to the first probe is observed at a level of from 10–20% of the average of all positive hybridizations on the solid support; and
   (v) cross hybridization is indicated if positive hybridization of the first color tag to the first probe, positive hybridization of the second color tag to the second probe, intermediate-positive hybridization of the second color tag to the first probe at a level of from 10–20% of the average of all positive hybridizations on the solid support, and intermediate-positive hybridization of the first color tag to the second probe at a level of from 10–20% of the average of all positive hybridizations on the solid support are observed.

* * * * *